US010426334B2

(12) United States Patent  
White et al.

(10) Patent No.: US 10,426,334 B2  
(45) Date of Patent: Oct. 1, 2019

(54) PORTABLE VISION TESTING APPARATUS

(71) Applicant: Global Vision 2020, Inc., Avon Lake, OH (US)

(72) Inventors: Joseph Kevin White, Easton, MD (US); Brian Everett, Ballwin, MO (US); Michael Swiney, St. Louis, MO (US); John Church, Neshkoro, WI (US); James Stephenson, Hoover, AL (US)

(73) Assignee: Global Vision 2020, Inc., Easton, MD (US)

( * ) Notice: Subject to any disclaimer, the term of this patent is extended or adjusted under 35 U.S.C. 154(b) by 120 days.

(21) Appl. No.: 15/545,814

(22) PCT Filed: Jan. 22, 2016

(86) PCT No.: PCT/US2016/014515  
§ 371 (c)(1),  
(2) Date: Jul. 24, 2017

(87) PCT Pub. No.: WO2016/122980  
PCT Pub. Date: Aug. 4, 2016

(65) Prior Publication Data  
US 2018/0020911 A1 Jan. 25, 2018

Related U.S. Application Data

(60) Provisional application No. 62/107,785, filed on Jan. 26, 2015, provisional application No. 62/197,987, filed on Jul. 28, 2015.

(51) Int. Cl.  
*A61B 3/04* (2006.01)  
*A61B 3/00* (2006.01)  
*A61B 3/028* (2006.01)

(52) U.S. Cl.  
CPC .............. *A61B 3/04* (2013.01); *A61B 3/0075* (2013.01); *A61B 3/028* (2013.01)

(58) Field of Classification Search  
USPC ...... 351/47, 49, 159.01, 222, 223, 224, 227, 351/245  
See application file for complete search history.

(56) References Cited

U.S. PATENT DOCUMENTS

| | | | |
|---|---|---|---|
| 4,500,180 | A | 2/1985 | Stevens |
| 7,159,984 | B2 | 1/2007 | Fukuma et al. |

(Continued)

FOREIGN PATENT DOCUMENTS

| | | | |
|---|---|---|---|
| JP | 7-163520 A | 6/1995 | |
| JP | 8-71041 A | 3/1996 | |

(Continued)

*Primary Examiner* — Mustak Choudhury  
(74) *Attorney, Agent, or Firm* — John H. Hornickel; Melissa Coombes; Michael J. Sambrook

(57) ABSTRACT

A vision testing apparatus is disclosed. The apparatus has a frame comprising a face plate with at least one eye shield having a viewing slot positioned in a viewing direction perpendicular to the face plate, at least one variable lens element including an outer rail and multiple regions of varying diopter power having a width that is equal to or greater than the width of the viewing slot of the eye shield, and adjustable controls for moving the variable lens element in a direction perpendicularly to the viewing direction along a plane of the face plate. The testing apparatus is portable and can be used in developing nations where visual acuity is not corrected because of lack of access to optometric care.

19 Claims, 7 Drawing Sheets

(56) References Cited

U.S. PATENT DOCUMENTS

| | | |
|---|---|---|
| 7,232,217 B2 | 6/2007 | Spivey |
| 7,980,690 B2 | 7/2011 | Baron van Asbeck |
| 8,668,338 B2 | 3/2014 | Johansson et al. |
| 2008/0074619 A1* | 3/2008 | Gisonna ............... A61B 3/0285 351/223 |
| 2014/0176909 A1* | 6/2014 | Spivey .................... A61B 3/04 351/223 |

FOREIGN PATENT DOCUMENTS

| | | |
|---|---|---|
| JP | 2001-170010 A | 6/2001 |
| JP | 2005-073924 A | 3/2005 |

* cited by examiner

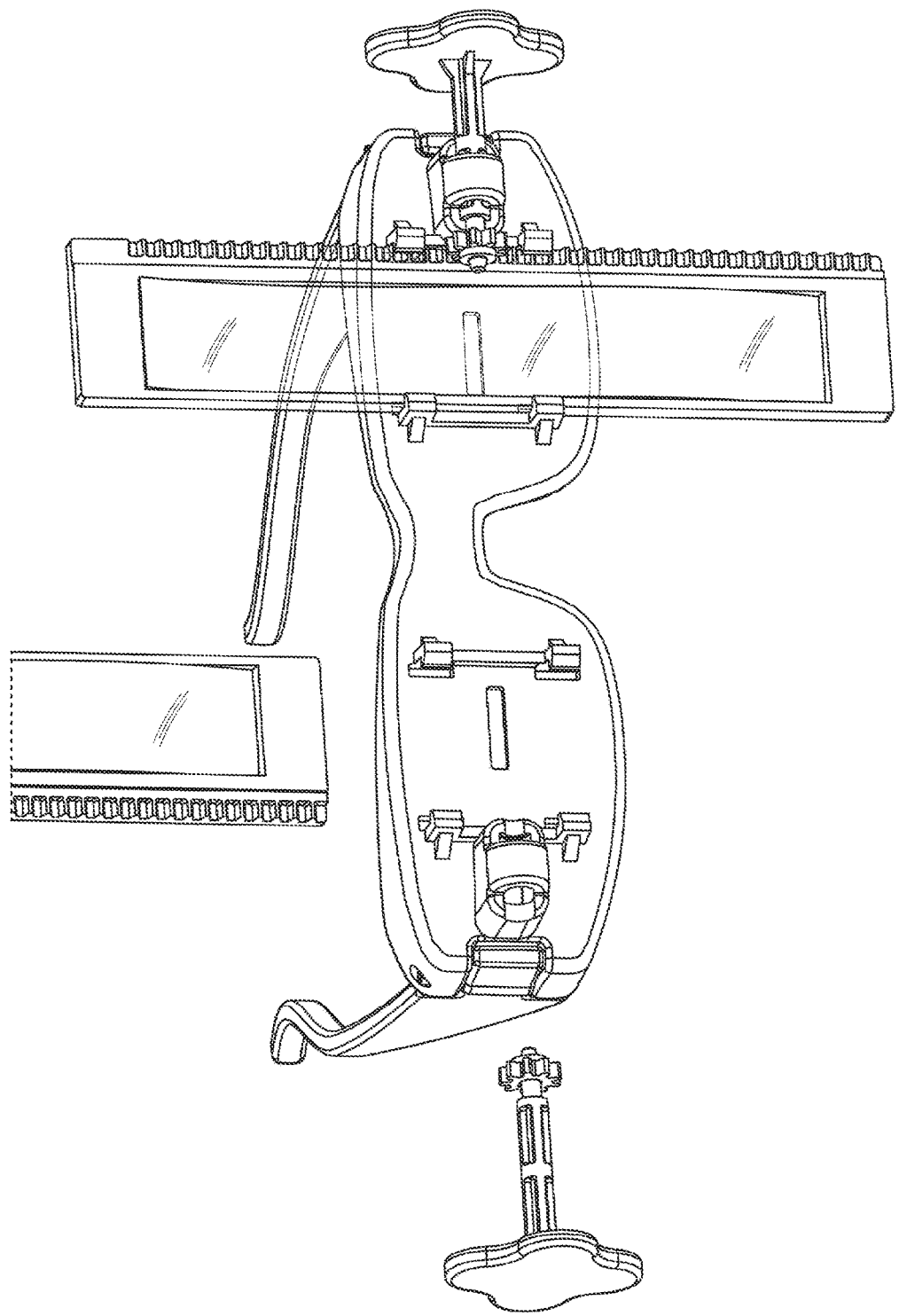

PORTABLE VISION TESTING APPARATUS

CLAIM OF PRIORITIES

This application claims priority from (a) U.S. Provisional Patent Application Ser. No. 62/107,785 filed on Jan. 26, 2015, which is incorporated by reference and (b) U.S. Provisional Patent Application Ser. No. 62/197,987 filed on Jul. 28, 2015, which is incorporated by reference.

FIELD OF THE INVENTION

This invention concerns an apparatus to test human visual acuity.

BACKGROUND OF THE INVENTION

Corrective eyeglasses are ubiquitous in the developed nations. As people progress from childhood to elderly years, their eyesight often change. Without corrected vision through the use of eyeglasses, many persons would have difficulty performing precision work, driving an automobile, reading, or looking at a computer screen.

In developing nations many people often have no direct access to a system of healthcare, including optometry. They live their lives with uncorrected vision because they have no access to vision correction diagnosis or eyeglasses, which can render distinct what was once naturally blurry.

SUMMARY OF THE INVENTION

What the world needs, especially in the developing nations, is an apparatus to correctly diagnose human visual acuity to 20-20 vision, or nearly so. The apparatus needs to provide a means for assessing the status of current vision of a person and what diopter corrections are needed to achieve 20-20 vision. To be useful in any human condition, the apparatus needs to be portable, handheld, and capable of functioning without electricity or other power source. The apparatus needs to be as useful in the Arctic as in the Amazon, or even Atlanta. The device also needs to be easy to use for both an examiner administering the test, and to the person whose eyes are being tested.

The present invention solves the problem of testing for human visual acuity in remote locations by providing a vision testing apparatus which has a frame, at least one variable lens element, and adjustable controls for moving the at least one variable lens element.

The frame has two corresponding temple arms that are each connected to a face plate, wherein the face plate comprises at least one eye shield having a viewing slot positioned in a viewing direction perpendicular to the face plate.

The at least one variable lens element has an outer rail and multiple regions of varying diopter power having a width that is equal to or greater than the width of the viewing slot of the eye shield, and each of the regions has a height that is equal to or greater than the height of the viewing slot.

The adjustable controls provide for moving of the at least one variable lens element in a direction perpendicularly to the viewing direction along a plane of the face plate, wherein the adjustable controls are mounted on the frame and comprise a mechanism to engage the outer rail of the at least one variable lens element.

The advantages of the vision testing apparatus are plentiful and further explained below in reference to the following drawings.

BRIEF DESCRIPTION OF THE DRAWING

FIG. 7 is a fourth depiction from the first Provisional Patent Application Ser. No. 62/107,785.

EMBODIMENTS OF THE INVENTION

Vision Testing Apparatus

Figure 1:
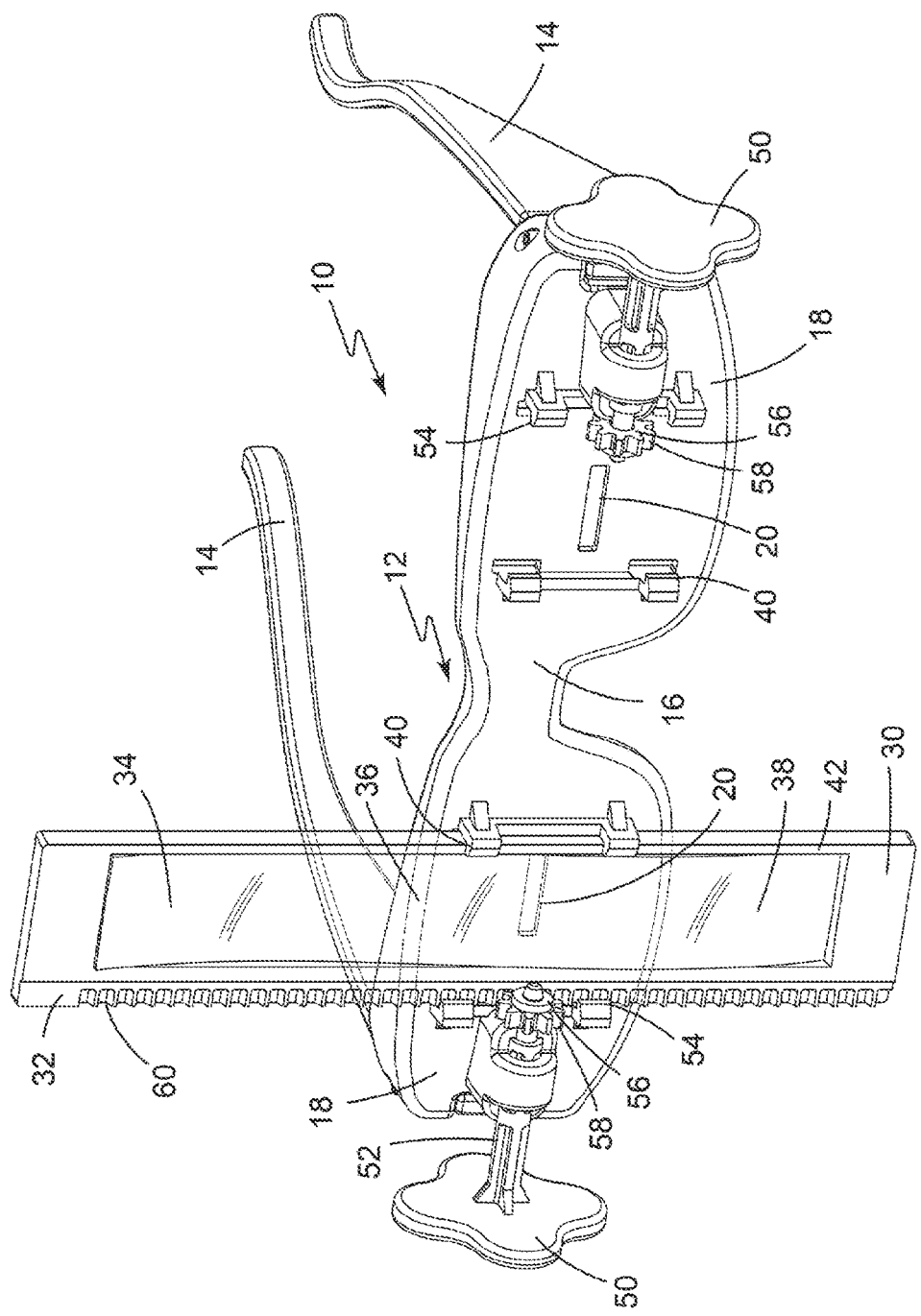
FIG. 1. is a perspective view of the vision testing apparatus.

In one embodiment of the invention, a vision testing apparatus 10 comprises a frame 12 comprising two corresponding temple arms 14 that are each connected to a face plate 16. The face plate comprises at least one eye shield 18 having a viewing slot 20 through the face plate 16 positioned in a viewing direction perpendicular to the face plate.

The vision testing apparatus 10 also comprises at least one variable lens element 30 which has an outer rail 32 and multiple regions 34, 36, and 38 of varying diopter power having a width that is equal to or greater than the width of the viewing slot 20 of the eye shield 18, and each of the regions 34, 36, and 38 has a height that is equal to or greater than the height of the viewing slot 20.

The vision testing apparatus 10 also had at least one adjustable control 50 for moving the at least one variable lens element 30 in a direction perpendicularly to the viewing direction along a plane of the face plate 16, wherein the adjustable control 50 is mounted on the frame 12 and comprises a mechanism 52 to engage the outer rail 32 of the at least one variable lens element 30.

The multiple regions 34, 36, 38, etc. of vision testing apparatus 10 are configured to vary in diopter power from +6.00 D to −15.00 D, allowing for determination of visual acuity correction within that range of diopter power. Preferably, as seen in the markings on variable lens element 30, each diopter power height in the multiple regions 34, 36, 38, etc. aligned with a viewing slot 20 on eye shield 18 of face place 16, such that a person wearing the frame 12 would see through slot 20 with a diopter correction of 34, 36, 38, etc. in quarter-diopter steps from +2.00 D to −6.00 D. Thus, for a particular quarter diopter, such as −2.50 D, the person seeing through slot 20 as corrected by diopter −2.50 D would identify whether the person can see clearly at a pre-determined distance either a letter, a number, a symbol, or the ubiquitous array of capital letter E pointed in a variety of all four directions.

Opposite the adjustable control 50 on eye shield 18 of face plate 16 is at least one alignment groove 40 that engages an inside rail 42 of the at least one variable lens element 30 in order that movement of element 30 from one diopter region 34 to a second diopter region 36 maintains proper alignment of element 30 against eye shield 18 and viewing slot 20 when vision correction is occurring.

Associated with outer rail 32 of lens element 30 is the adjustable control 50 with mechanism 52 mounted on eye shield 18 of face plate 16 and over top of an alignment slot 54 that engages the outer rail 32 of the at least one variable lens element 30 in order that movement of element 30 from one diopter region 34 to a second diopter region 36 also maintains proper alignment of element 30 against eye shield 18 and viewing slot 20 when vision correction is occurring.

One embodiment of the mechanism 52 can be a gear wheel 56 with teeth 58 to rotationally mesh with teeth 60 projecting from the outside rail 32 of lens element 30 and the face place 16.

One embodiment of the vision testing apparatus 10 can include a conventional side shield (not shown) on least one of the two corresponding temple arms 14 to reduce ambient light from a direction different from the viewing direction.

As seen in FIG. 1, one lens element 30 is inserted into groove 40 and slot 54 to be configured to move vertically using outer rail 32 and inside rail 42 along eye shield 18 in order that each diopter region 34, 36, 38, etc. can cover the viewing slot. Also as seen in FIG. 1, the second or left eye shield 18 with viewing slot 20 can be vacant while one or the right eye is tested. Alternatively, as seen in FIG. 2, two lens elements 30 can be aligned in the left and right eye shields for concurrent determination of proper diopter settings for visual acuity correction.

As often occurs in optometric examination, one eye can be tested before the second eye, followed by a final test using both eyes. The lens elements 30 are detachable from eye shields 18 by turning of the adjustable controls 50 on each eye shield.

As seen in FIG. 1, the face plate 16 comprises two eye shields 18, and each of the eye shields 18 has a respective viewing slot 20. Slot 20 on right eye shield 18 is readily seen in FIG. 1, while slot 20 on left eye shield 18 is shown in dotted lines because lens element 30 covers that left slot 20.

Figure 2:
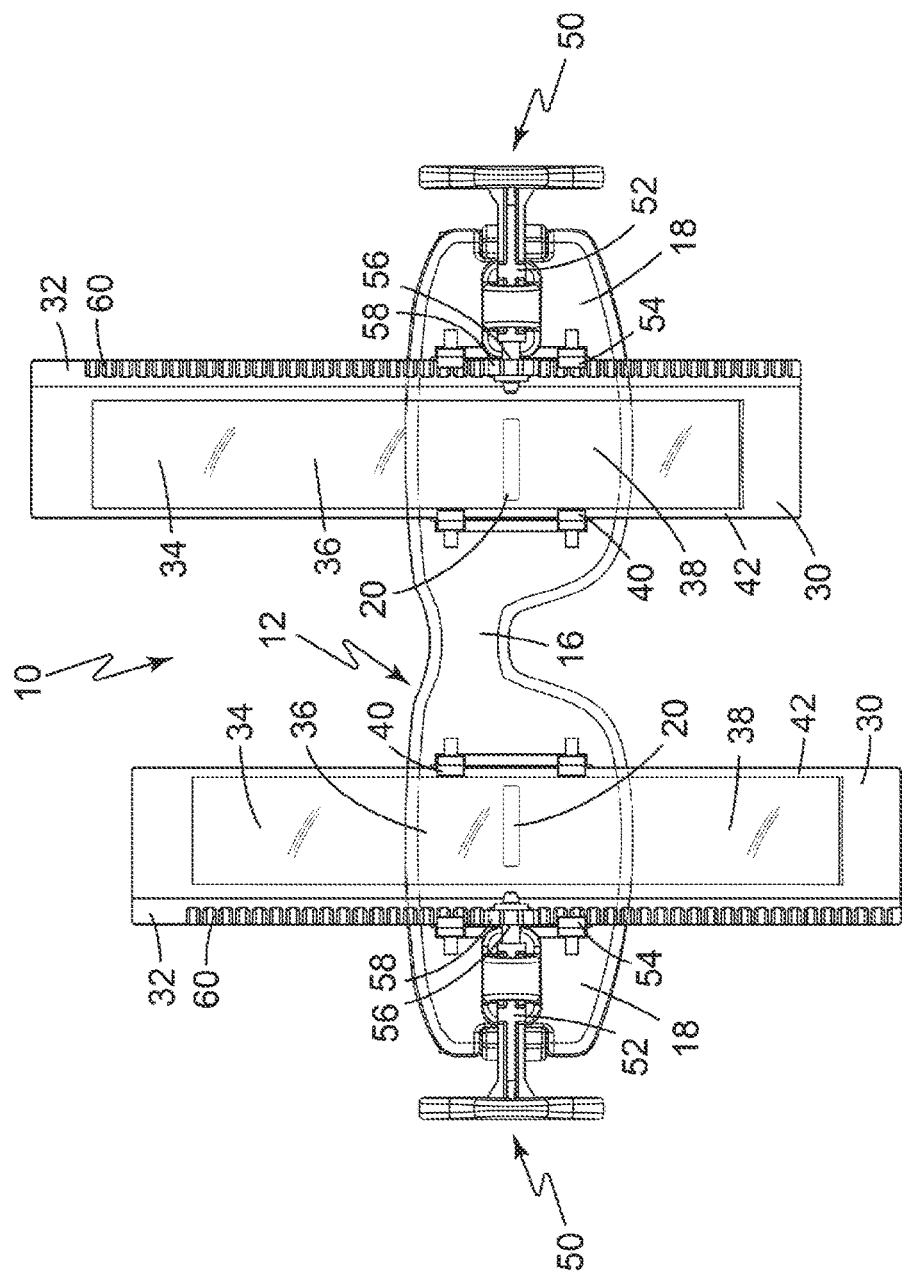
FIG. 2 is a front view of the vision testing apparatus.

FIG. 2 shows a front view of vision correction apparatus 10 with two lens elements 30 aligned on face place 16 at left and right eye shields 18 such that one region 34, 36, or 38 of diopter correction is positioned over viewing slot 20. Left and right adjustable controls 50, using one embodiment left and right mechanisms 52 of left and right gears 56 with teeth 58 to mesh with teeth 60 on left and right outer rails 32 of left and right lens elements 30.

As stated previously, the elements 30 can be adjusted one at a time or concurrently depending on how the vision correction examination is conducted. With a person unable to see through frame 12 in the viewing direction except through left and right viewing slots 20 on left and right eye shields, respectively, and with each diopter setting 34, 36, or 38 covering viewing slot, the person can either inform the examiner to adjust the dial 50 or self-adjust the dial 50 until the viewing chart is in best possible focus.

The adjustment for both left and right eyes continues with adjustment of left and right lens elements 30, sequentially or concurrently, until the person under examination either informs the examiner which individual left and right diopter setting is in clearest focus or self-adjusts the dials 50 to self-determine the clearest focus possible within the diopter range being tested for each eye.

Each diopter region 34, 36, 38, etc. on each lens element 30 can be a step-wise transition or a progressive transition, so long as each tooth 60 on outer rail 32 of a lens element 30 meshes precisely with a tooth 56 on mechanism 52 of the adjustable control 50. For a progressive transition, the multiple regions 34, 36, 38, etc. continuously vary in diopter power from a high convergence region to a high divergence region. For a step-wise transition, the multiple regions 34, 36, 38, etc. vary in diopter power using a segmented lens, wherein each of the multiple regions 34, 36, 38, etc. of the segmented lens each have discrete diopter powers.

In another embodiment, the face plate 16 comprises an alignment groove 40 that meshes with teeth 60 also projecting from the inside rail 42 of a lens element 30. To demonstrate this embodiment, the left lens element 30 in FIG. 2 is shown with teeth 60 on inside rail 42.

Figure 3:
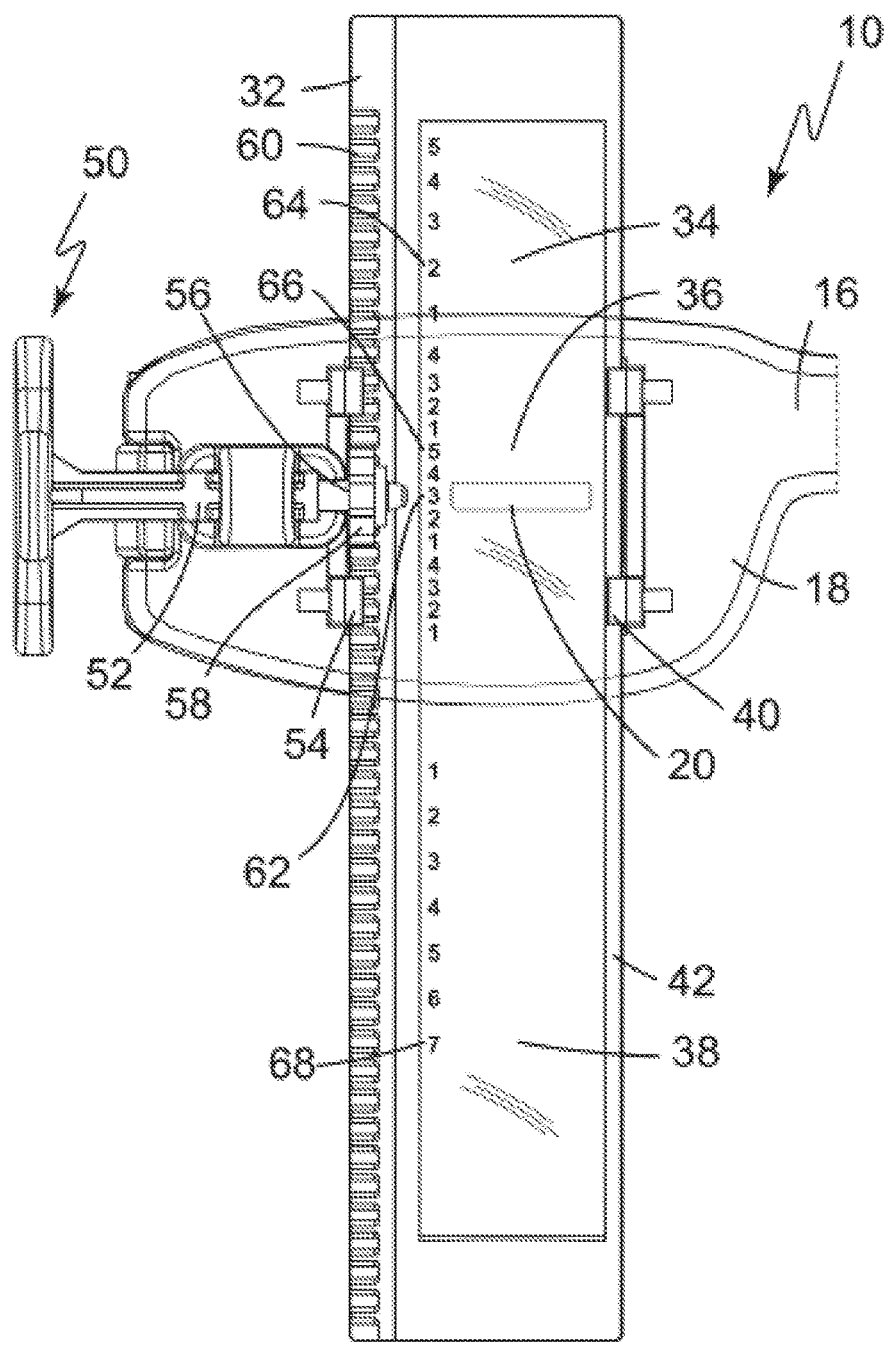
FIG. 3 is partial front view of the vision testing apparatus focused on the adjustable controls capable of moving a variable lens element in a direction perpendicularly to the viewing direction along a plane of the face plate.
Figure 4:
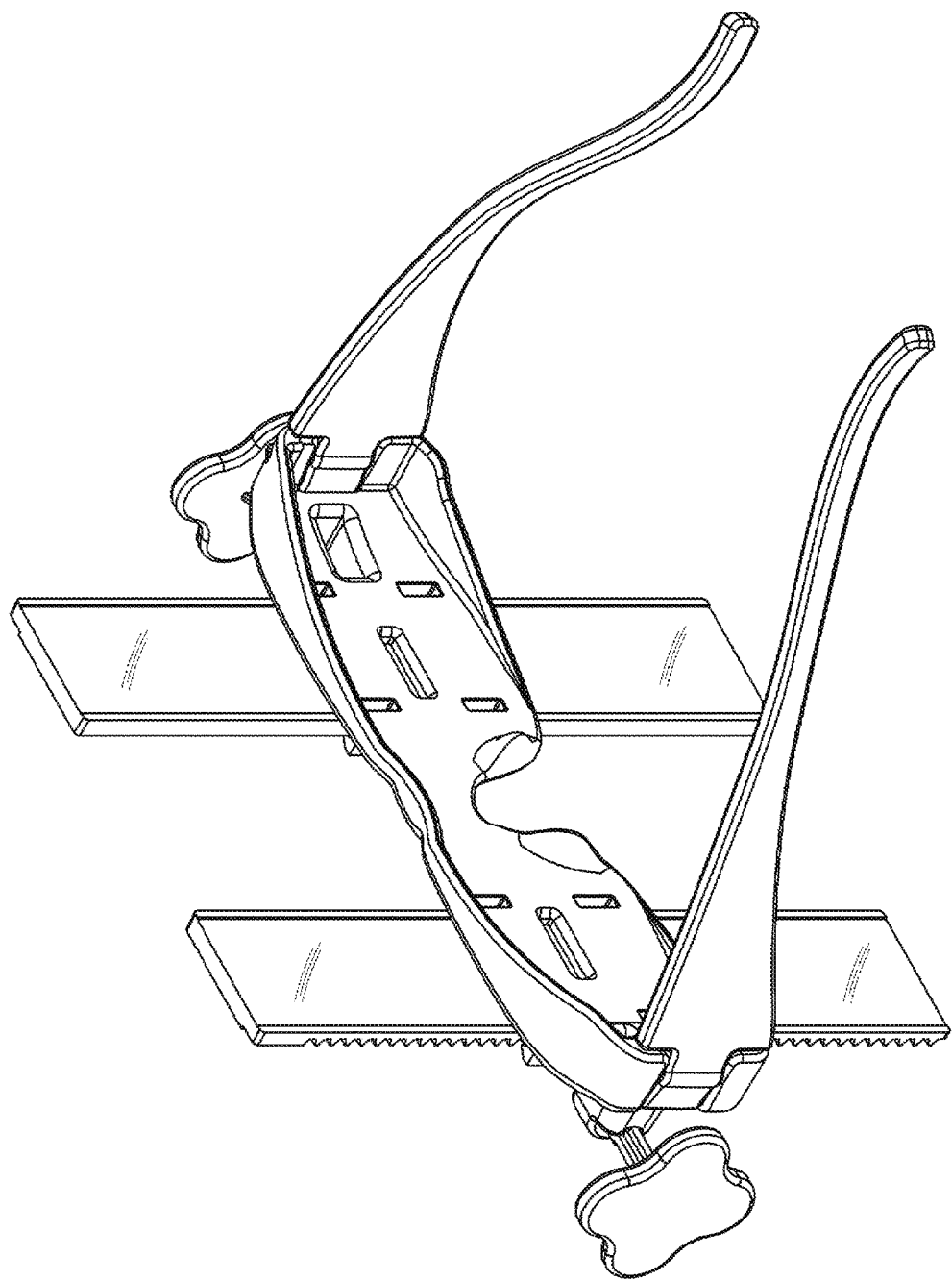
FIG. 4 is a depiction from the first Provisional Patent Application Ser. No. 62/107,785.
Figure 5:
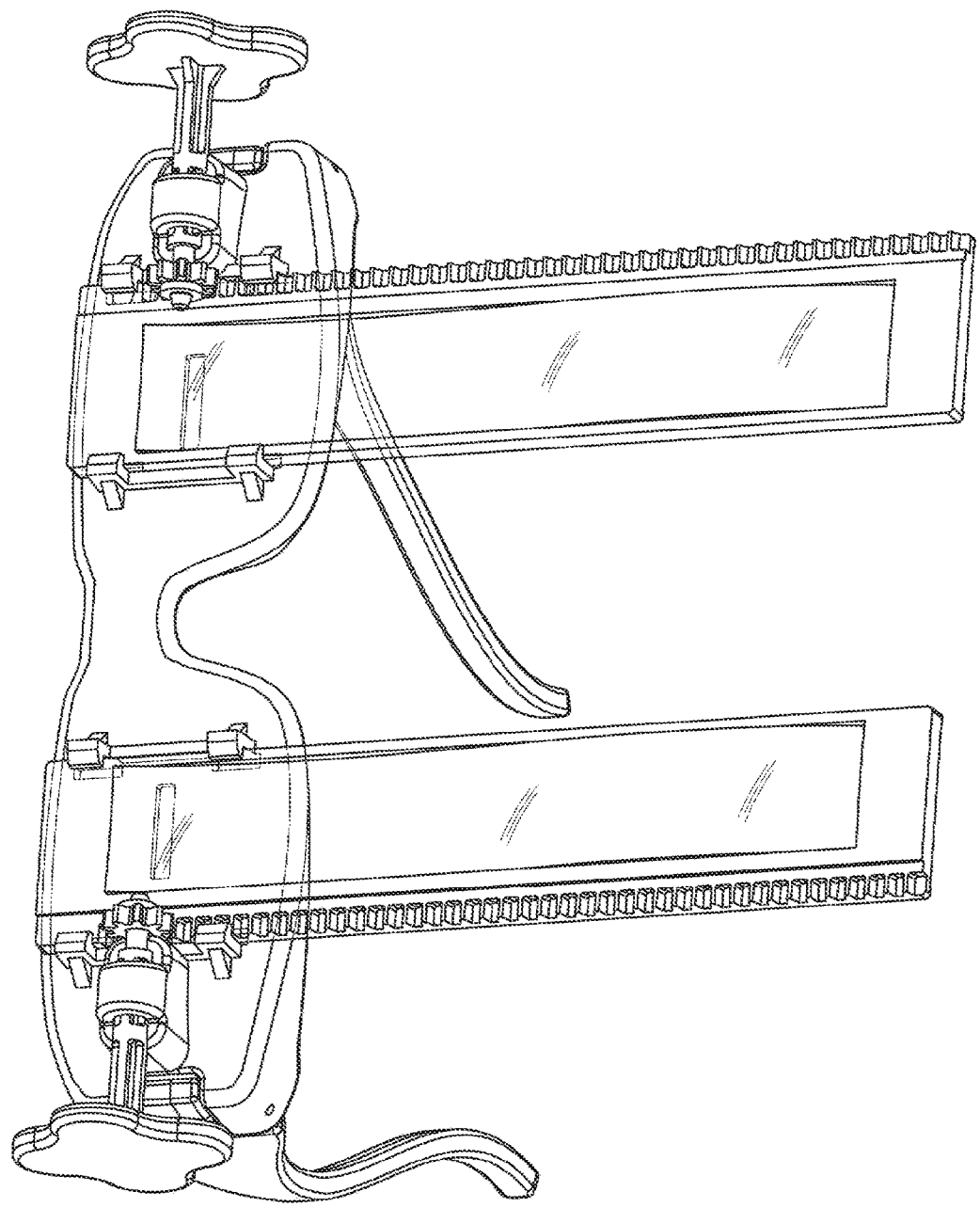
FIG. 5 is a second depiction from the first Provisional Patent Application Ser. No. 62/107,785.
Figure 6:
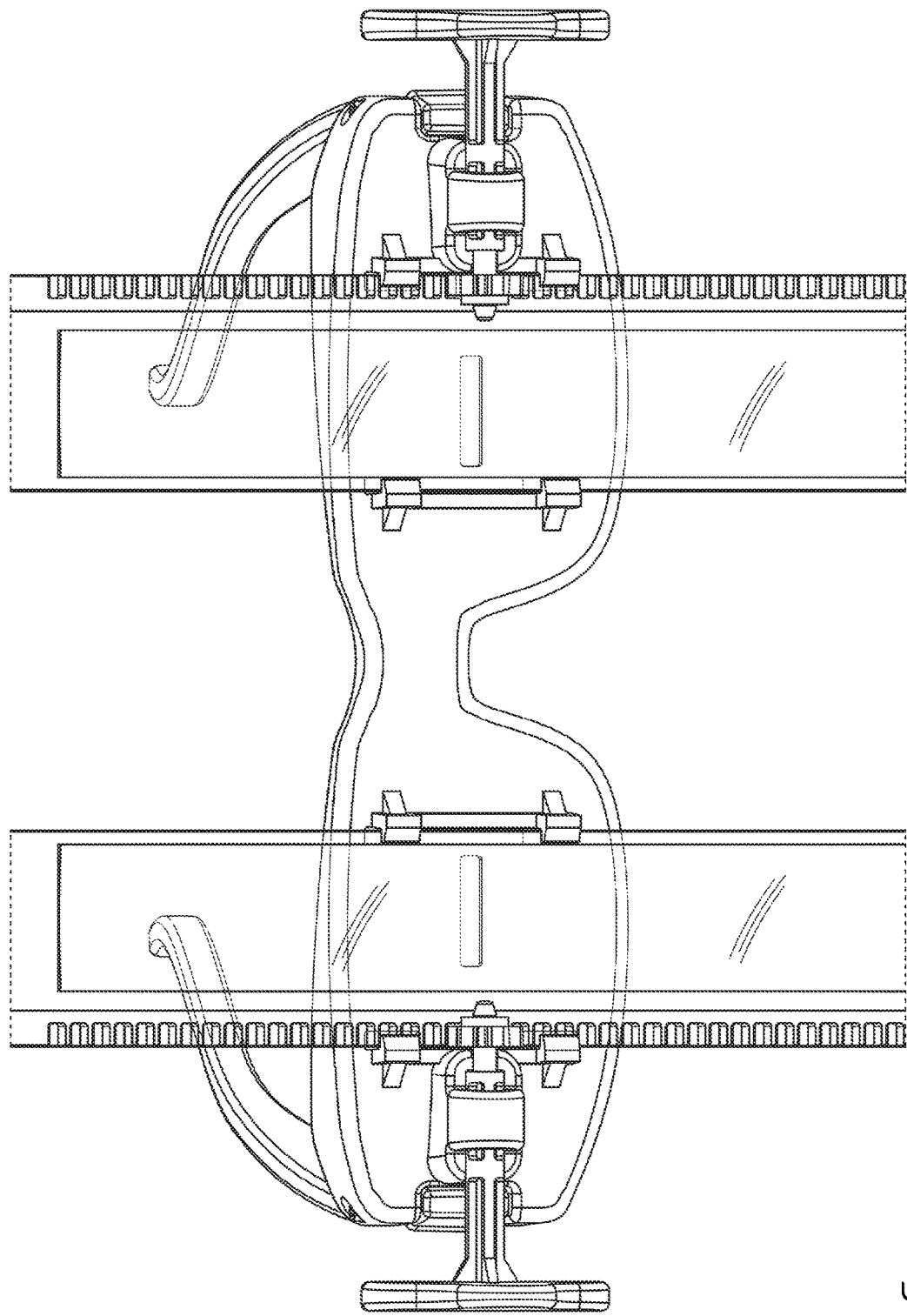
FIG. 6 is a third depiction from the first Provisional Patent Application Ser. No. 62/107,785.

FIG. 3 shows an embodiment of the vision correction apparatus 10 where at least one variable lens element 30 comprises visual indicators 62 for each of the multiple regions 34, 36, 38, etc. of diopter power. In FIG. 3, the visual indicator 62 shows a diopter of −2.00 D for region 36 of right lens element 20. Optionally, each diopter value 64, 66, 68, etc. is indicated on inside rail 42 of lens element 30.

In another embodiment, a lens element 30 having multiple regions 34, 36, 38, etc. of different diopter powers have for each diopter power a thickness substantially constant in a direction perpendicular to the viewing direction. This constancy across the diopter setting provides a consistent correction across the corresponding viewing slot 20 on eye shield. Thus, this embodiment does not make acuity correction for astigmatism, only spherical power. However, other embodiments of this invention can utilize different lens elements wherein the thickness varies in a direction perpendicular to the viewing direction in order to measure for any astigmatism.

In another embodiment, the vision testing apparatus 10 comprises:

(a) a frame 12 comprising two corresponding temple arms 14 that are each connected to a face plate 16, wherein the face plate 16 comprises two eye shields 18 each having a viewing slot 20 positioned in a viewing direction perpendicular to the face plate 16;

(b) two variable lens elements 30 each comprising an outer rail 32 and multiple regions 34, 36, 38, etc. of varying diopter power having a width that is equal to or greater than the width of the viewing slot 20 of the eye shield 18, and each of the regions 34, 36, 38, etc. has a height that is equal to or greater than the height of the viewing slot 20; and (c) adjustable controls 50 for independently moving each of the two variable lens elements 30 in a direction perpendicularly to the viewing direction along a plane of the face plate 16, wherein the adjustable controls 50 are mounted on the frame 16 and comprise a mechanism 52 to engage the outer rail 32 of the at least one variable lens element 30.

In this alternative embodiment, at least one of the variable lens elements 30 can be a progressive lens or a segmented lens, wherein each of the multiple regions 34, 36, 38, etc. of the segmented lens each have discrete diopter powers.

The multiple regions 34, 36, 38, etc. of varying diopter power for each of the two variable lens elements 30 are identical in diopter range.

For any embodiment of the invention, the face plate 16 can use a flexible nose bridge to assist the use of testing frame 12 on persons of a variety of nose shapes. Moreover, that testing frame 12 can have indicators to identify which eyeglasses frame to choose for the corrective eyeglasses, based on nose shape.

The present invention also involves a method of configuring a set of prescription eyeglasses suitable for a person comprising the steps of:

(1) measuring the vision of a person to determine a corrective diopter power for an eye by using a vision testing apparatus 10 comprising (a) a frame 12 comprising two corresponding temple arms 14 that are each connected to a face plate 16, wherein the face plate 16 comprises at least one eye shield 18 having a viewing slot 20 positioned in a viewing direction perpendicular to the face plate 16;

(b) at least one variable lens element 30 comprising an outer rail 32 and multiple regions 34, 36, 38, etc. of varying power having a width that is equal to or greater than the width of the viewing slot 20 of the eye shield 18, and each of the regions has a height that is equal to or greater than the height of the viewing slot; and (c) adjustable controls 50 for moving the at least one variable lens element 30 in a direction perpendicularly to the viewing direction along a plane of the face plate 16, wherein the adjustable controls are mounted on the frame 12 and comprise a mechanism 52 to engage the outer rail 32 of the at least one variable lens element 30;

(2) selecting a lens having a diopter power that corresponds to the corrective diopter power measured;

(3) assembling the set of prescription eyeglasses with at least the lens selected; and (4) optionally, performing the measuring, selecting, and assembling steps for a second eye.

Materials Employed

The vision correction apparatus 10 can be made from a variety of metallic, ceramic, wooden, or polymeric materials depending on the purposes of each part of the apparatus. Each lens element 30 needs to be both sturdy to move precisely within the adjustable control 50 and the frame 12 and in the diopter regions 34, 36, 38, etc. be translucent approaching transparency in order that the person looking through a viewing slot 20 on an eye shield 18 can clearly see through the lens element diopter region(s) to determine whether the object at a distance is in focus. The other parts of the vision correction apparatus 10 can be opaque, especially each eye shield 18 in order the person looking in the viewing direction can only see through a viewing slot 20 and one of the diopter regions on a lens element 30.

Of the various possible materials, polymeric materials offer the most versatility and do not rot, shatter, or rust as to wooden, glass, or metallic materials.

A person having ordinary skill in the art without undue experimentation can select the polymeric materials to be molded into the various parts of apparatus 10. Companies such as PolyOne Corporation have a variety of polymeric materials from which that person can choose appropriate polymers for appropriate parts. For example, a suitable polymer material known for clarity and sturdiness for a lens element can be a molding grade of a polycarbonate or a polyester. Likewise, a suitable polymer material known for opacity and precision molding for the frame 16, eye shields 18, adjustable controls 50 can be a rigid polyvinyl chloride or polyamide. The flexible arms can be a plasticized polymer such as flexible polyvinyl chloride. The flexible nose bridge can be a thermoplastic elastomer of relatively soft durometer hardness, such as a styrenic block copolymer compound.

Optional Polymeric Additives

The various polymeric materials can include functional additives to further provide good processing techniques or end-use performance in a rugged environment.

The polymeric materials used in the present invention can include conventional plastics additives in an amount that is sufficient to obtain a desired processing or performance property for the compound. The amount should not be wasteful of the additive nor detrimental to the processing or performance of the compound. Those skilled in the art of thermoplastics compounding, without undue experimentation but with reference to such treatises as *Plastics Additives Database* (2004) from Plastics Design Library (elsevier.com), can select from many different types of additives for inclusion into the compounds of the present invention.

Non-limiting examples of optional additives include adhesion promoters; biocides (antibacterials, fungicides, and mildewcides), anti-fogging agents; anti-static agents; bonding, blowing and foaming agents; dispersants; fillers and extenders; fire and flame retardants and smoke suppressants; impact modifiers; initiators; lubricants; micas; pigments, colorants and dyes; plasticizers; processing aids; release agents; silanes, titanates and zirconates; slip and anti-blocking agents; stabilizers; stearates; ultraviolet light absorbers; viscosity regulators; waxes; and combinations of them.

Processing

The preparation of polymeric compounds to make the vision correction apparatus 10 of the present invention is uncomplicated. The compound of the present can be made in batch or continuous operations.

Mixing in a continuous process typically occurs in an extruder that is elevated to a temperature that is sufficient to melt the polymer matrix with addition either at the head of the extruder or downstream in the extruder of the solid ingredient additives. Extruder speeds can range from about 50 to about 500 revolutions per minute (rpm), and preferably from about 100 to about 300 rpm. Typically, the output from the extruder is pelletized for later extrusion or molding into polymeric articles.

Mixing in a batch process typically occurs in a Banbury mixer that is also elevated to a temperature that is sufficient to melt the polymer matrix to permit addition of the solid ingredient additives. The mixing speeds range from 60 to 1000 rpm and temperature of mixing can be ambient. Also, the output from the mixer is chopped into smaller sizes for later extrusion or molding into polymeric articles.

Subsequent extrusion or molding techniques are well known to those skilled in the art of thermoplastics polymer engineering. Without undue experimentation but with such references as "Extrusion, The Definitive Processing Guide and Handbook"; "Handbook of Molded Part Shrinkage and Warpage"; "Specialized Molding Techniques"; "Rotational Molding Technology"; and "Handbook of Mold, Tool and Die Repair Welding", all published by Plastics Design Library (elsevier.com), one can make articles of any conceivable shape and appearance using polymeric compounds.

Considering the embodiments of the apparatus 10 of this invention, the various parts of frame 12, lens element 30, and adjustable controls 50 are likely to be molded, most particularly using injection molding techniques customarily used in the thermoplastic engineering arts.

USEFULNESS OF THE INVENTION

The vision correction apparatus 10 of the present invention can provide a handheld, non-powered testing device to measure visual acuity of a person by manual movement of a lens element 30 using adjustable control 50 from one diopter region 34 to another diopter region 36 or 38. By being limited in the viewing direction of only looking through a viewing slot 20 and through a diopter region 34, 36, 38, etc., a person's vision can be corrected by identifying the diopter settings for a corrective lens.

With apparatus 10, a vision chart placed at a pre-determined distance, and a supply of lens suitable for insertion into eyeglass frames, a person far from modern optometric equipment or professional assistance can have her or his vision corrected.

It is contemplated that the supply of lenses can fit either the left or the right housing of an eyeglass frame. It is also contemplated that the eyeglass frame is capable of adjustment to fit any number of facial structures, particularly eye width, arm length, and nose bridge. With a supply of lenses suitable for the likely lenses needed for proper vision correction, a person with apparatus 10 can serve persons away from optometric care for weeks without replenishment.

What most in the developed world consider normal, accurate vision, can now become normal to persons in the developing world as well.

APPENDIX

The following text was the text of the first Provisional Patent Application Ser. No. 62/107,785 filed on Jan. 26, 2015

Self/Patient Adjusting Progressing Lens Refractometer
"U-See"
Patent Application
Date: 26 Jan. 2015
Inventor: Joseph Kevin White
Disclaimer: No federal funds were used to develop this invention Background: This invention is for use in the determination of lens power needed for a wearer to correct refractive power deficiencies (i.e.: short sighted, long sited—myopia, hyperopia and presbyopia.). The only existing device that currently helps the wearer correct their vision is a fluid filled pair of glasses (AdSpecs) or an Alvarez device (FocusSpecs), but these do not necessarily give a prescription (power), but are converted into a wearable pair of glasses.

Summary: This invention will have as its sole purpose, the determining of the required power of the patient eyes, to correct refractive error through self-refraction. Using progressive lenses, powered with a wide range of power from negative to positive (potentially +6 to –6), the wearer will be able to dial in his or her correct prescription, which can then be used to make a pair of conventional glasses. The application for this invention is for use in the developing world where standard optometric practices are impossible, or at the least, impractical.

Description: The invention is a small wearable device that is placed on the face of the patient, much like a conventional pair of glasses, which the patient can look through. In front of each eye is a progressive lens that is mounted in such a way that it can be moved with a dial that the patient can gradually turn, passing the various powers directly in front of the eye. The patient looks through the lens as he/she turns the dial, and stops when the image across the room (i.e.: eye chart approximately 4 meters away) comes into best focus. The position on the lens is calibrated to a scale on the edge of the lens that correlates with the prescriptive power on that portion of the lens. This reading will represent the patient's refractive prescription requirements for the tested eye. See illustrations below (FIGS. 4-7).

Claims: I claim that I invented this device through extensive use of fluid filled lenses on various missions to the developing world (all in Africa). I claim that this device replicates the experience of a fluid filled self-refraction, but in a device that minimizes moving parts, can be calibrated and ruggedized, and can be used continually for the sole purpose of getting refractive data on a patient in order to get that patient the correct power prescription for the issuing of a pair of conventional glasses that will correct the patients vision.

The above embodiments do not limit the invention. The claims follow.

What is claimed is:

1. A vision testing apparatus comprising:
  a frame comprising two corresponding temple arms that are each connected to a face plate, wherein the face plate comprises at least one eye shield having a viewing slot positioned in a viewing direction perpendicular to the face plate;
  a variable lens element having a width that is equal to or greater than the width of the viewing slot, the variable lens element comprising:
    an outer rail; and
    multiple regions of varying diopter power, each region of the multiple regions of varying diopter power having a specific curvature associated with a specific diopter value and a height that is equal to or greater than the height of the viewing slot; and
  an adjustable control for moving the variable lens element in a direction perpendicular to the viewing direction along a plane of the face plate, wherein the adjustable control is mounted on the frame and comprises a mechanism to engage the outer rail of the variable lens element; and
  wherein the face plate further comprises both:
    (a) at least one alignment groove configured to house an inside rail of the variable lens element; and
    (b) an alignment slot configured to house the outer rail of the variable lens element, wherein the alignment slot comprises an opening though which at least a portion of the adjustable control engages the outer rail to move the variable lens element perpendicular to the viewing direction along the plane of the face plate.

2. The vision testing apparatus of claim 1, wherein the multiple regions vary in power from +6.00 D to –15.00 D.

3. The vision testing apparatus of claim 1, wherein the multiple regions are in quarter-diopter steps from +6.00 D to –6.00 D.

4. The vision testing apparatus of claim 1, wherein the adjustable control comprises a gear wheel with teeth to rotationally mesh with teeth projecting from the outer rail of the variable lens element.

5. The vision testing apparatus of claim 1, wherein at least one of the two corresponding temple arms comprises a side shield to reduce ambient light from a direction different from the viewing direction.

6. The vision testing apparatus of claim 1, wherein the face plate comprises two eye shields, and each of the eye shields has a respective viewing slot.

7. The vision testing apparatus of claim 1, further comprising two variable lens elements corresponding to the two eye shields.

8. The vision testing apparatus of claim 1, wherein the variable lens element is a progressive lens.

9. The vision testing apparatus of claim 8, wherein the multiple regions of the progressive lens continuously vary in diopter power from a high convergence region to a high divergence region.

10. The vision testing apparatus of claim 1, wherein the variable lens element is a segmented lens.

11. The vision testing apparatus of claim 10, wherein each segment of the segmented lens has a discrete diopter power.

12. The vision testing apparatus of claim 1, wherein the variable lens element comprises visual indicators for each of the multiple regions of varying diopter power.

13. The vision testing apparatus of claim 1, wherein the adjustable control comprises visual indicators for each of the multiple regions of varying diopter power.

14. The vision testing apparatus of claim 1, wherein a diopter power within each of the multiple regions of varying diopter power is substantially constant in a direction perpendicular to the viewing direction.

15. A vision testing apparatus comprising:
a frame comprising two corresponding temple arms that are each connected to a face plate, wherein the face plate comprises two eye shields each having a viewing slot positioned in a viewing direction perpendicular to the face plate;
two variable lens elements each having a width that is equal to or greater than the width of respective viewing slots, the two variable lens elements each comprising:
an outer rail; and
multiple regions of varying diopter power, each region of the multiple regions of varying diopter power having a specific curvature associated with a specific diopter value and a height that is equal to or greater than the height of the viewing slot; and
two adjustable controls, each of the two adjustable controls configured to independently move respective variable lens elements in a direction perpendicular to the viewing direction along a plane of the face plate, wherein the two adjustable controls are mounted on the frame and each comprise a mechanism to engage the outer rail of the respective variable lens elements, and
wherein the face plate further comprises:
(a) at least one alignment groove configured to house an inside rail of each of the two variable lens elements; and
(b) an alignment slot configured to house the outer rail of the respective variable lens element, wherein the alignment slot comprises an opening through which at least a portion of the adjustable controls engage the outer rail to move the respective variable lens element perpendicular to the viewing direction along the plane of the face plate.

16. The vision testing apparatus of claim 15, wherein each of the two variable lens elements comprises a progressive lens.

17. The vision testing apparatus of claim 15, wherein the multiple regions of varying diopter power for each of the two variable lens elements are identical, and wherein the face plate comprises a nose bridge, wherein the nose bridge is flexible.

18. The vision testing apparatus of claim 15, wherein each of the two adjustable controls comprise a gear wheel with teeth to rotationally mesh with teeth projecting from the outer rail of the respective variable lens element.

19. A method of configuring a set of prescription eyeglasses suitable for a person comprising:
measuring the vision of a person to determine a corrective diopter power for an eye by using a vision testing apparatus comprising:
a frame comprising two corresponding temple arms that are each connected to a face plate, wherein the face plate comprises:
an eye shield having a viewing slot positioned in a viewing direction perpendicular to the face plate;
an alignment groove configured to house an inner rail of a variable lens element; and
an alignment slot configured to house an outer rail of the variable lens element;
the variable lens element having a width that is equal to or greater than the width of the viewing slot and comprising:
multiple regions of varying power, each region of the multiple regions of varying diopter power having a specific curvature associated with a specific diopter value and each a height that is equal to or greater than the height of the viewing slot; and
an adjustable control for moving the variable lens element in a direction perpendicular to the viewing direction along a plane of the face plate, wherein the adjustable control is mounted on the frame and comprise a mechanism to engage the outer rail of the variable lens element through an opening in the alignment slot;
selecting a lens for the set of prescription eyeglasses based on the corrective diopter power; and
assembling the set of prescription eyeglasses with at least the lens selected-based on the corrective diopter power.

* * * * *